(12) United States Patent
Nakamura (10) Patent No.: US 12,279,788 B2
(45) Date of Patent: Apr. 22, 2025

(54) END-POINT DETECTION METHOD AND MEDICAL DEVICE CONTROLLER AND TREATMENT SYSTEM WITH END-POINT DETECTION, PARTICULARLY FOR ELECTROSURGERY

(71) Applicant: OLYMPUS MEDICAL SYSTEMS CORP., Tokyo (JP)

(72) Inventor: Kotaro Nakamura, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 777 days.

(21) Appl. No.: 17/531,931

(22) Filed: Nov. 22, 2021

(65) Prior Publication Data

US 2022/0273332 A1  Sep. 1, 2022

Related U.S. Application Data (60) Provisional application No. 63/154,156, filed on Feb. 26, 2021.

(51) Int. Cl.
  *A61B 17/32*  (2006.01)
  *A61B 5/01*  (2006.01)
  *A61B 17/00*  (2006.01)

(52) U.S. Cl.
  CPC ........ *A61B 17/320092* (2013.01); *A61B 5/01* (2013.01); *A61B 2017/00084* (2013.01); *A61B 2017/00415* (2013.01); *A61B 2017/320095* (2017.08)

(58) Field of Classification Search
  CPC ........ A61B 17/320092; A61B 18/1445; A61B 2017/00022; A61B 2017/00084; A61B 2017/00415; A61B 2017/320095; A61B 2018/00601; A61B 2018/0063; A61B 2018/00666; A61B 2018/00684; A61B 2018/00702; A61B 2018/00708; A61B 2018/00791; A61B 2018/00875; A61B 2018/00898; A61B 5/01; A61B 5/02007; A61B 5/4836; A61B 5/6847; A61B 5/6876
  See application file for complete search history.

(56) References Cited

U.S. PATENT DOCUMENTS

2018/0280084 A1* 10/2018 Hancock ............ A61B 18/1815
2020/0205878 A1*  7/2020 Wang .................... F04B 51/00

* cited by examiner

*Primary Examiner* — Tigist S Demie
(74) *Attorney, Agent, or Firm* — Morgan, Lewis & Bockius LLP (57) ABSTRACT

A method for controlling a medical device for treating a biological tissue includes controlling the treatment procedure based on the heat capacity of the biological tissue being treated as observed by the medical device. A change in the rate of change of heat capacity from a decreasing rate to an increasing rate or exceeding a maximum threshold value of rate of change of the heat capacity indicates completion, e.g., cutting or sealing. The heat capacity of the biological tissue may be estimated by determining a ratio of energy input to an end-effector of the medical device over a sampling interval to a change in temperature of the biological tissue over that sampling interval. The method may be incorporated into a controller for a medical device for treating a biological tissue.

16 Claims, 7 Drawing Sheets

END-POINT DETECTION METHOD AND MEDICAL DEVICE CONTROLLER AND TREATMENT SYSTEM WITH END-POINT DETECTION, PARTICULARLY FOR ELECTROSURGERY

RELATED APPLICATION DATA

This application is based on and claims priority under 35 U.S.C. § 119 to U.S. Provisional Application No. 63/154,156, filed Feb. 26, 2021, the entire contents of which are incorporated herein by reference.

TECHNICAL FIELD

The systems, devices and methods disclosed herein are directed to medical devices, and in particular to medical devices, treatment systems, and methods used for electrosurgical procedures.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Electrosurgical devices using different end-effectors for providing heat to a biological tissue are used in various procedures such as, for example, cauterizing a blood vessel, welding tissues or lumens, or sealing blood vessels or other lumens. Some of the commonly used end-effectors for such procedures produce heat using, for example, ultrasonic vibration or high frequency electrical energy.

Because of the physical environment in which the procedures are performed, visual confirmation of an end-point of the procedure is difficult or impossible. For example, in many instances, the sealing of the blood vessels or cutting of the tissue is performed during a minimally invasive procedure such as a laparoscopic procedure, where the clinician has no line-of-sight to the area of treatment. Even if a line-of-sight is provided, for example, by way of a camera, the size of the blood vessel or the tissue to be cut as well as the presence of bodily fluids can make it difficult to detect the end-point visually with a high level of certainty.

Many electrosurgical devices, therefore, use other measures such as, for example, ultrasonic or electrical impedance of the biological tissue, or ultrasonic or electrical resonance frequency, for detecting the end-point. However, because of the presence of the bodily fluids, and because the surrounding biological tissue often has similar physical properties as the biological tissue being operated upon, the changes in impedance or resonance frequency at the end-point may be relatively small in magnitude, and therefore, difficult to detect.

Without an accurate estimation of the end-point of the procedure, it is difficult to control the energy output at the site of the end-effector causing undesirable rise in temperature at the site of the procedure or resulting in undesirable effects on the biological tissue surrounding the site of the procedure. Moreover, continuing the procedure after the end-point leads to wastage of time which can be critical for patient safety. In these situations patient safety may be compromised.

SUMMARY

In view of the above-noted issues, detecting an end-point of the procedure becomes important for avoiding undesired effects as well as for improving the speed and efficiency of the procedure. For example, accurate determination that only a desired portion of the biological tissue is cut can avoid cutting of surrounding biological tissue. Similarly, determination that sealing of a blood vessel is completed can avoid overheating and consequent damage to the blood vessel and surrounding biological tissue. Advantageously, accurate determination of the end-point of the procedure may also save the clinician from spending excess time by continuing to perform a procedure when it is already completed.

It would be advantageous to have improved techniques to more accurately determine an end-point of an electrosurgical procedure so as to better control the input of energy to the biological tissue on which the procedure is being performed. An accurate determination of the end-point of the electrosurgical procedure is an important factor in improving patient safety as well as improving the speed and efficiency of the procedure.

In general, the presently disclosed end-point detection methods (and devices and systems incorporating the same) utilizes a change in the heat capacity during the treatment procedure to monitor the progress of the procedure, to determine the state of the biological tissue, and to determine an end point of the procedure. During a procedure on a biological tissue, such as during electrosurgery, the mass of the biological tissue changes as the amount of water in the biological tissue evaporates and causes the heat capacity of the biological tissue to change. Thus, one can be determine that a procedure, such as sealing of biological tissue by high frequency energy or cutting of biological tissue by ultrasonic vibration energy, is complete based on the observed heat capacity. In one instance, the value of heat capacity observed by the medical device changes from decreasing to increasing, indicating that the procedure on the biological tissue has been complete, e.g., cutting or sealing. In another instance, a maximum threshold value of heat capacity is set and the value of heat capacity observed by the medical device exceeding that threshold indicates that the procedure on the biological tissue has been complete, e.g., cutting or sealing. Advantageously, a procedure with dynamic monitoring of heat capacity improves the efficiency of the treatment procedures, the quality of the cutting or sealing, and minimizes the damage to the biological tissue.

Accordingly, a method for controlling a medical device for treating a biological tissue comprises estimating a heat capacity of the biological tissue, determining a state of the biological tissue based on the estimated heat capacity, and controlling the medical device based on the determined state of the biological tissue.

In one aspect of the present disclosure, a method for controlling a medical device for treating a biological tissue may include determining an in-process heat capacity of the biological tissue during a time period of application of applied energy to the biological tissue, wherein the applied energy is ultrasonic energy or electrical energy. A state of the biological tissue is determined based on the in-process heat capacity. The medical device is controlled based on the state of the biological tissue.

In some embodiments, the medical device includes an end-effector configured to operate on the biological tissue, and wherein determining the in-process heat capacity of the biological tissue is based on a parameter associated with electrical energy input to the end-effector and a temperature of the biological tissue.

In some embodiments, the medical device includes an end-effector configured to operate on the biological tissue, and wherein determining the in-process heat capacity of the biological tissue includes determining a ratio of energy input to the end-effector over a sampling interval to a change in temperature of the biological tissue over that sampling interval.

In some embodiments, the change in temperature of the biological tissue is determined based on an output of a temperature sensor associated with the medical device.

In some embodiments, the change in temperature of the biological tissue is determined by estimating, based on a first set of parameters, a residual energy associated with (i) a prior amount of electrical power provided to the medical instrument, (ii) a prior amount of electrical power consumed by the medical instrument, (iii) a prior amount of electrical power applied to the end-effector, (iv) a prior amount of electrical power consumed by the end-effector, or (v) a combination thereof. Based on the first set of parameters, a change in energy of the end-effector is determined based on (i) a current amount of electrical power provided to the medical instrument, (ii) a current amount of electrical power consumed by the medical instrument, (iii) a current amount of electrical power applied to the end-effector, (iv) a current amount of electrical power consumed by the end-effector, or (v) a combination thereof. A residual temperature of the end-effector associated with the residual energy is estimated. A change in temperature of the end-effector associated with the change in energy is determined.

In some embodiments, the change in temperature of the biological tissue is determined by estimating a residual energy associated with a prior application of base energy to the end-effector based on a first set of parameters. An amount of electric power that is converted to heat at the end-effector is estimated based on the first set of parameters. A current temperature at the end-effector is estimated based on: (i) the residual energy, (ii) the amount of electric power provided to the end-effector, and (iii) a time for which the electric power is provided to the end-effector.

In some embodiments, the first set of parameters includes one or more of a mass of a treatment portion of the end-effector, a shape of the treatment portion of the end-effector, a size of the treatment portion of the end-effector, and a specific heat of the treatment portion of the end-effector.

In some embodiments, determining the state of the biological tissue includes determining the state of the biological tissue based on a change in the in-process heat capacity.

In some embodiments, the medical device includes an end-effector configured to heat the biological tissue. Determining the state of the biological tissue includes detecting an end-point of a procedure being performed on the biological tissue by the end-effector. Controlling the medical device includes stopping application of applied energy to the biological tissue upon detection of the end-point of the procedure.

In some embodiments, the applied energy is ultrasonic energy and the end-effector is configured to heat the biological tissue by providing ultrasonic vibration to the biological tissue. The end-point of the procedure includes completion of cutting of the biological tissue. The completion of cutting of the biological tissue is determined when a rate of change of the heat capacity of the biological tissue changes from a decreasing rate to an increasing rate.

In some embodiments, the applied energy is ultrasonic energy and the end-effector is configured to heat the biological tissue by providing ultrasonic vibration to the biological tissue. The end-point of the procedure includes completion of cutting of the biological tissue. The completion of cutting of the biological tissue is determined when a rate of change of the heat capacity of the biological tissue exceeds a heat capacity threshold value.

In some embodiments, the applied energy is ultrasonic energy and the end-effector is configured to heat the biological tissue by providing ultrasonic vibration to the biological tissue. The end-point of the procedure includes completion of cutting of the biological tissue. The completion of cutting of the biological tissue is determined when (i) a rate of change of the heat capacity of the biological tissue changes from a decreasing rate to an increasing rate and (ii) the rate of change of the heat capacity of the biological tissue exceeds a heat capacity threshold value.

In some embodiments, the applied energy is electrical energy and the end-effector is configured to heat the biological tissue by providing high frequency electrical energy to the biological tissue. The end-point of the procedure includes completion of sealing of the biological tissue. The completion of sealing of the biological tissue is determined when a rate of change of the heat capacity of the biological tissue exceeds a heat capacity threshold value.

In some embodiments, the method may further include notifying a user that the end-point of the procedure has been reached.

In another aspect, a controller for a medical device for treating a biological tissue may include a processor configured to implement any of the methods described herein.

In a further aspect, a controller for a medical device for treating a biological tissue, the controller may include a processor configured to determine an in-process heat capacity of the biological tissue during a time period of application of applied energy to the biological tissue, wherein the applied energy is ultrasonic energy or electrical energy. The processor determines a state of the biological tissue based on the in-process heat capacity, and controls the medical device based on the state of the biological tissue.

In some embodiments, the medical device includes an end-effector configured to operate on the biological tissue, and wherein determining the in-process heat capacity of the biological tissue is based on a parameter associated with electrical energy input to the end-effector and a temperature of the biological tissue.

In some embodiments, the medical device includes an end-effector configured to operate on the biological tissue, and wherein determining the in-process heat capacity of the biological tissue includes determining a ratio of energy input to the end-effector over a sampling interval to a change in temperature of the biological tissue over that sampling interval. the change in temperature of the biological tissue is determined based on an output of a temperature sensor associated with the medical device.

In some embodiments, the change in temperature of the biological tissue is determined by estimating, based on a first set of parameters, a residual energy associated with (i) a prior amount of electrical power provided to the medical instrument, (ii) a prior amount of electrical power consumed by the medical instrument, (iii) a prior amount of electrical power applied to the end-effector, (iv) a prior amount of electrical power consumed by the end-effector, or (v) a combination thereof. Based on the first set of parameters, a change in energy of the end-effector is determined based on (i) a current amount of electrical power provided to the medical instrument, (ii) a current amount of electrical power consumed by the medical instrument, (iii) a current amount of electrical power applied to the end-effector, (iv) a current amount of electrical power consumed by the end-effector, or (v) a combination thereof. A residual temperature of the end-effector associated with the residual energy is estimated. A change in temperature of the end-effector associated with the change in energy is determined.

In some embodiments, the change in temperature of the biological tissue is determined by estimating a residual energy associated with a prior application of base energy to the end-effector based on a first set of parameters. An amount of electric power that is converted to heat at the end-effector is estimated based on the first set of parameters. A current temperature at the end-effector is estimated based on: (i) the residual energy, (ii) the amount of electric power provided to the end-effector, and (iii) a time for which the electric power is provided to the end-effector.

In some embodiments, the first set of parameters includes one or more of a mass of a treatment portion of the end-effector, a shape of the treatment portion of the end-effector, a size of the treatment portion of the end-effector, and a specific heat of the treatment portion of the end-effector.

In some embodiments, determining the state of the biological tissue includes determining the state of the biological tissue based on a change in the in-process heat capacity.

In some embodiments, the medical device includes an end-effector configured to heat the biological tissue. Determining the state of the biological tissue includes detecting an end-point of a procedure being performed on the biological tissue by the end-effector. Controlling the medical device includes stopping application of applied energy to the biological tissue upon detection of the end-point of the procedure.

In some embodiments, the applied energy is ultrasonic energy and the end-effector is configured to heat the biological tissue by providing ultrasonic vibration to the biological tissue. The end-point of the procedure includes completion of cutting of the biological tissue. The completion of cutting of the biological tissue is determined when a rate of change of the heat capacity of the biological tissue changes from a decreasing rate to an increasing rate.

In some embodiments, the applied energy is ultrasonic energy and the end-effector is configured to heat the biological tissue by providing ultrasonic vibration to the biological tissue. The end-point of the procedure includes completion of cutting of the biological tissue. The completion of cutting of the biological tissue is determined when a rate of change of the heat capacity of the biological tissue exceeds a heat capacity threshold value.

In some embodiments, the applied energy is ultrasonic energy and the end-effector is configured to heat the biological tissue by providing ultrasonic vibration to the biological tissue. The end-point of the procedure includes completion of cutting of the biological tissue. The completion of cutting of the biological tissue is determined when (i) a rate of change of the heat capacity of the biological tissue changes from a decreasing rate to an increasing rate and (ii) the rate of change of the heat capacity of the biological tissue exceeds a heat capacity threshold value.

In some embodiments, the applied energy is electrical energy and the end-effector is configured to heat the biological tissue by providing high frequency electrical energy to the biological tissue. The end-point of the procedure includes completion of sealing of the biological tissue. The completion of sealing of the biological tissue is determined when a rate of change of the heat capacity of the biological tissue exceeds a heat capacity threshold value.

In some embodiments, the processor is further configured to initiate a notification that the end-point of the procedure being performed has been reached.

In a further aspect, a medical device includes a medical instrument including an end-effector configured to contact the biological tissue and to transmit heat to the contacted biological tissue, and a power source configured to provide electric power to the medical instrument. The medical device further includes any of the controllers described herein.

A non-transitory computer-readable medium having instructions stored thereon, which when implemented by a processor cause the processor to execute any of the methods described herein.

Additional features and advantages will be set forth in the description that follows, and in part will be apparent from the description, or may be learned by practice of the invention. The objectives and other advantages of the disclosed input device will be realized and attained by the structure particularly pointed out in the written description and claims thereof as well as the appended drawings.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

In FIGS. 4A and 4B, the time on the X-axis is synchronized.

Throughout all of the drawings, dimensions of respective constituent elements are appropriately adjusted for clarity. For ease of viewing, in some instances only some of the named features in the figures are labeled with reference numerals.

DETAILED DESCRIPTION

Accordingly, one aspect of the present disclosure describes a method for controlling a medical device for treating a biological tissue by accurately estimating the end-point of an electrosurgical procedure. The method may include determining a heat capacity of the biological tissue and determining a state of the biological tissue based on the determined heat capacity. The medical device is then controlled based on the determined state of the biological tissue. The heat capacity is determined based on a parameter associated with electrical energy input to an end-effector of the medical device and a temperature of the biological tissue. The end-point of the procedure being performed using the medical device is determined based on the state of the biological tissue, which may, in turn, be determined based a value of or a rate of change in value of heat capacity of the biological tissue.

In another aspect, present disclosure further relates to a medical device, per se, which operates based on the method for accurately estimating the end-point of the electrosurgical procedure.

In some embodiments, the medical device may provide applied energy—for example, ultrasonic energy or electrical energy, such as high frequency electrical energy—to the biological tissue during a treatment procedure. High frequency, as used herein, refers to a frequency in a range from about 100 kHz to about 5 MHz. Thus, depending on the specific application, a device may supply electrical energy to the biological tissue by applying a voltage ata frequency of, e.g., 100 kHz, 150 kHz, 200 kHz, 250 kHz, 300 kHz, 350 kHz, 400 kHz, 450 kHz, 500 kHz, 600 kHz, 700 kHz, 800 kHz, 900 kHz, 1000 kHz, 1500 kHz, 2000 kHz, 2500 kHz, 3000 kHz, 3500 kHz, 4000 kHz, 4500 kHz, 5000 kHz, or any frequency between any two of these frequencies.

The term "patient," as used herein, comprises any and all organisms and includes the term "subject." A patient can be a human or an animal.

Medical Device for Treating a Biological Tissue

Figure 1:
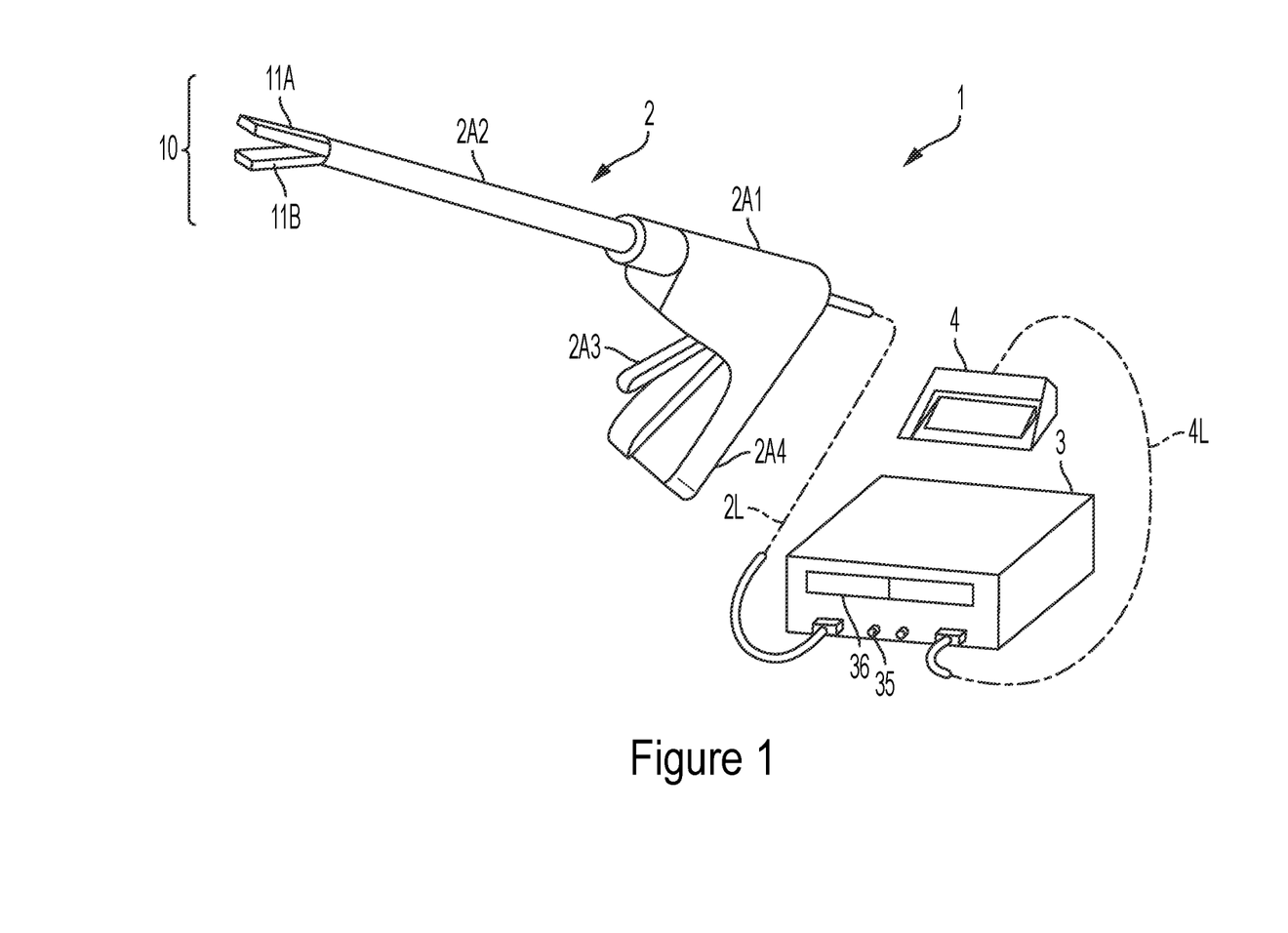
FIG. 1 shows a schematic of a medical device for treating a biological tissue, in accordance with an embodiment of the present disclosure.

FIG. 1 shows a schematic of a medical device for treating a biological tissue, in accordance with an embodiment of the present disclosure. As shown in FIG. 1, the medical device 1 for treating a biological tissue is provided with an instrument 2, a controller 3 having a processor and an actuation switch 4. The instrument 2 may be, for example, a surgical operation energy inosculation apparatus used for welding biological tissue, such as in an abdominal cavity through an abdominal wall, or incising, such as in an open surgery procedure or laparoscopy. In some embodiments, the instrument 2 may seal the biological tissue as the cutting process finishes so as to prevent bleeding when the biological tissue is cut.

The treatment instrument 2 has a grip 2A1, a shaft 2A2, and a treatment section constituted by an end-effector 10 such as, for example, an openable or pivoting pair of grasping sections (including a first grasping section 11A and a second grasping section 11B) for grasping biological tissue to perform treatment. The grasping sections as whole are also referred to herein as the "treatment portion" or the "treatment section" of the medical instrument. Note that, hereinafter, at time of mentioning each of components having a same function and having reference numerals with A and B attached to ends of the reference numerals, respectively, the symbol A or B may be omitted. For example, each of the first grasping section 11A and the second grasping section 11B may be referred to as the grasping section.

The grip 2A1 is connected to the controller 3 via a cable 2L. The grip 2A1 has an opening/closing actuator 2A3, such as a trigger, for a surgeon to operate opening and closing of the treatment section is in such a shape that the surgeon can easily clasp, for example, in a substantially L shape. The opening/closing actuator 2A3 is arranged at one end of the grip 2A1 and is integrated with the treatment section to transmit operation of the opening/closing actuator 2A3 to the treatment section. On the other side of the grip 2A1, a grasping portion 2A4 is provided for a clinician to grasp when operating the instrument 2.

Those of skill in the art will appreciate that while the drawings show the end-effector 10 of the instrument 2 as having a grasper, other types of end-effectors are contemplated within the scope of the claims. For example, in some embodiments, the end-effector may be a pin, a peg or a blade that vibrates long its axis at ultrasonic frequencies so as to pierce the biological tissue for cutting it.

Figure 2:
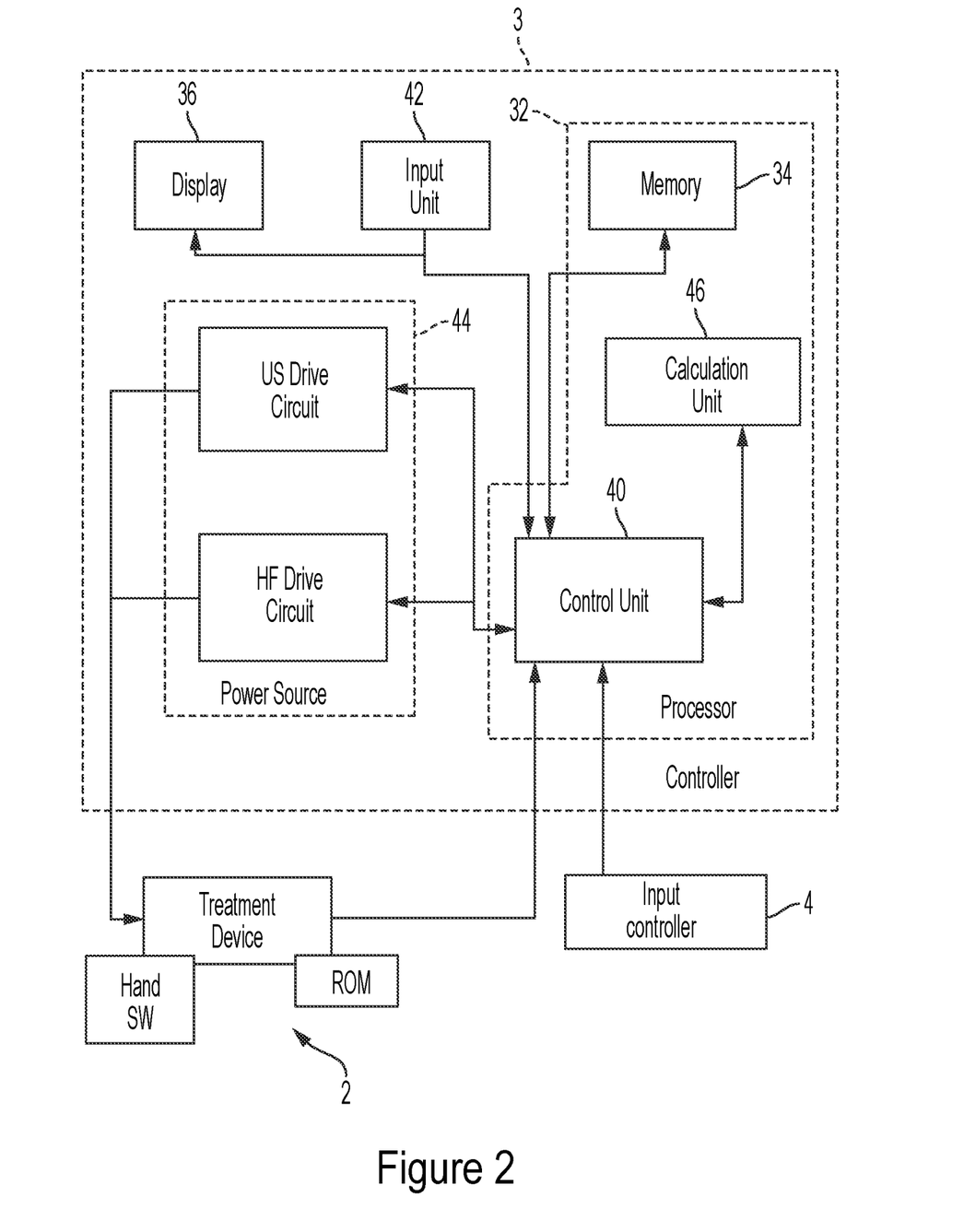
FIG. 2 shows a schematic of a controller in accordance with an embodiment of the present disclosure.

FIG. 2 shows a schematic of a controller in accordance with an embodiment of the present disclosure. The controller 3 may include a processor 32, a display 36, an input unit 42, and a power source 44.

The processor 32 may include a memory 34, a calculation unit 46 and a control unit 40. The calculation unit 46 and the control unit 40 are formed of an integrated circuit including a CPU (Central Processing Unit), an ASIC (Application Specific Integrated Circuit) or an FPGA (Field Programmable Gate Array). The calculation unit 46 and the control unit 40 may be formed a single integrated circuit, or may be formed of a plurality of integrated circuits.

In some embodiments, various parameters used for estimating an end-point of a procedure being performed such as, for example, the current temperature of biological tissue on which the treatment is being performed, the heat capacity of the biological tissue, the current temperature of the end-effector, the heat capacity of the end-effector, the thermal resistance of the end-effector, the thermal conductivity of the end-effector, or a contact area between the body of the biological tissue and the end-effector, may be stored in memory 34, e.g., in a look-up table stored in the memory 34.

The look-up table may include the values of the corresponding parameters for different end-effectors. Similarly, the look-up table may include values of the corresponding parameters for different types of biological tissues. For example, the look-up table may include the parameters for muscle tissue, adipose tissue, blood vessels, intestinal wall, or other biological tissue types. In some embodiments, the heat capacity of the biological tissue is estimated based on a change in temperature of the biological tissue. Calculating the change in temperature may require estimating a current temperature. In such embodiments, for example, estimating the current temperature may include determining the type of biological tissue on which the procedure is being performed, and determining the corresponding parameter values in the look-up table for estimating the current temperature. Alternatively, the procedure name may be used as the basis for entry into the look-up table.

The calculation unit 46 is configured to compute an estimated heat capacity as well as other parameters that are needed for computing the estimated heat capacity. The control unit 40 is configured to control the power source 44 and the display 36 based on the commands provided by the processor 32 using the parameters computed by the calculation unit 46.

In some embodiments, the data related to the various parameters is a value of the contact area calculated using size and shape of the end-effector, and how the end-effector is used (e.g., related to the procedure) and this data may be stored in the memory in advance. In addition, as the contact area changes as the end-effector grasps and regrasps biological tissue during the medical procedure, the various parameters can also correspondingly change during the procedure, and having the data for the various parameters readily available in memory allows for dynamic updating during the medical procedure.

The display 36 that displays treatment conditions and the like, and a setting operation section 35 for the surgeon to set the treatment conditions and the like, are on a front panel of the controller 3. In some embodiments, a foot switch 4 may be connected to the controller 3 via a cable 4L. The clinician may turn the power output from the controller 3 to the treatment instrument 2 ON or OFF by an input controller 4, such as by pressing a pedal of a foot switch of the input controller 4. The foot switch is not an essential component and any input controller can be utilized, such as a switch or the like which the clinician operates by hand or other alternative input controller.

In some embodiments, the controller 3 includes a processor 32 which controls the application of power to the instrument 2 via the power source 44 so as to maintain safe and effective operation of the end-effector 10. In some embodiments, the processor 32 may override the input provided by the clinician (e.g., through the input controller 4) for turning the power to the instrument 2 ON or OFF.

To control the power input to the instrument 2, the processor 32 may determine a state of the biological tissue using the methods described herein, and determine whether the procedure has been completed based on the state of the biological tissue, at for example, the calculation unit 46.

In some embodiments, the controller 3 may also include an alarm for providing a confirmation or alert based on the state of the biological tissue and/or based on the completion of the procedure. The alarm may be audible (e.g., a speaker (not shown)), visual (e.g., display 36), audiovisual, haptic or a combination thereof. In such embodiments, when the processor 32 determines, that the end-point of the procedure has been reached, the processor 32 via the control unit 40 may cause the alarm to be turned on so as to provide a confirmation signal to the clinician. On the other hand, in some embodiments, the processor 32 may cause the alarm to be turned on if the clinician attempts to disengage the end-effector or turn off power to the end-effector before the procedure has completed.

In some embodiments, the control unit 40 may cause the display 36 to display the state of the biological tissue on which the procedure is being performed. For example, the end-point of the procedure can be displayed in the display section along with the current state of the biological tissue. Thus, a clinician may be able to visually estimate whether the end-point of the procedure has reached and how far the procedure is from completion.

In some embodiments, the state of the biological tissue can be determined based on a parameter associated with the biological tissue, and the procedure is determined to be complete when the parameter reaches a preset value. The preset value for the parameter can be set by the clinician, for example, before beginning the procedure, using the setting operation section 35, which may be input to the processor via the input unit 42. In some embodiments, the preset value of the parameter can be set or calculated based on a different parameter set by the clinician before beginning the procedure or during the procedure using the setting operation section 35. In other embodiments, the preset value of the parameter can be set or calculated based on inputs monitored or detected during the procedure itself. Example parameters associated with the biological tissue include the heat capacity of the biological tissue being treated as observed by the medical device. For example, a change in the rate of change of heat capacity from a decreasing rate to an increasing rate or exceeding a maximum threshold value of rate of change of the heat capacity can indicate completion, e.g., cutting or sealing, of the procedure.

Relatedly, depending on the procedure, the state of the biological tissue and consequently an end-point of the procedure being performed can be determined based on a change in the heat capacity of the biological tissue, and more particularly, (i) based on a change in the rate of change in the heat capacity of the biological tissue, (ii) a valued of the rate of change in the heat capacity of the biological tissue exceeding a threshold value, or (iii) a combination of (i) and (ii).

Figure 3:
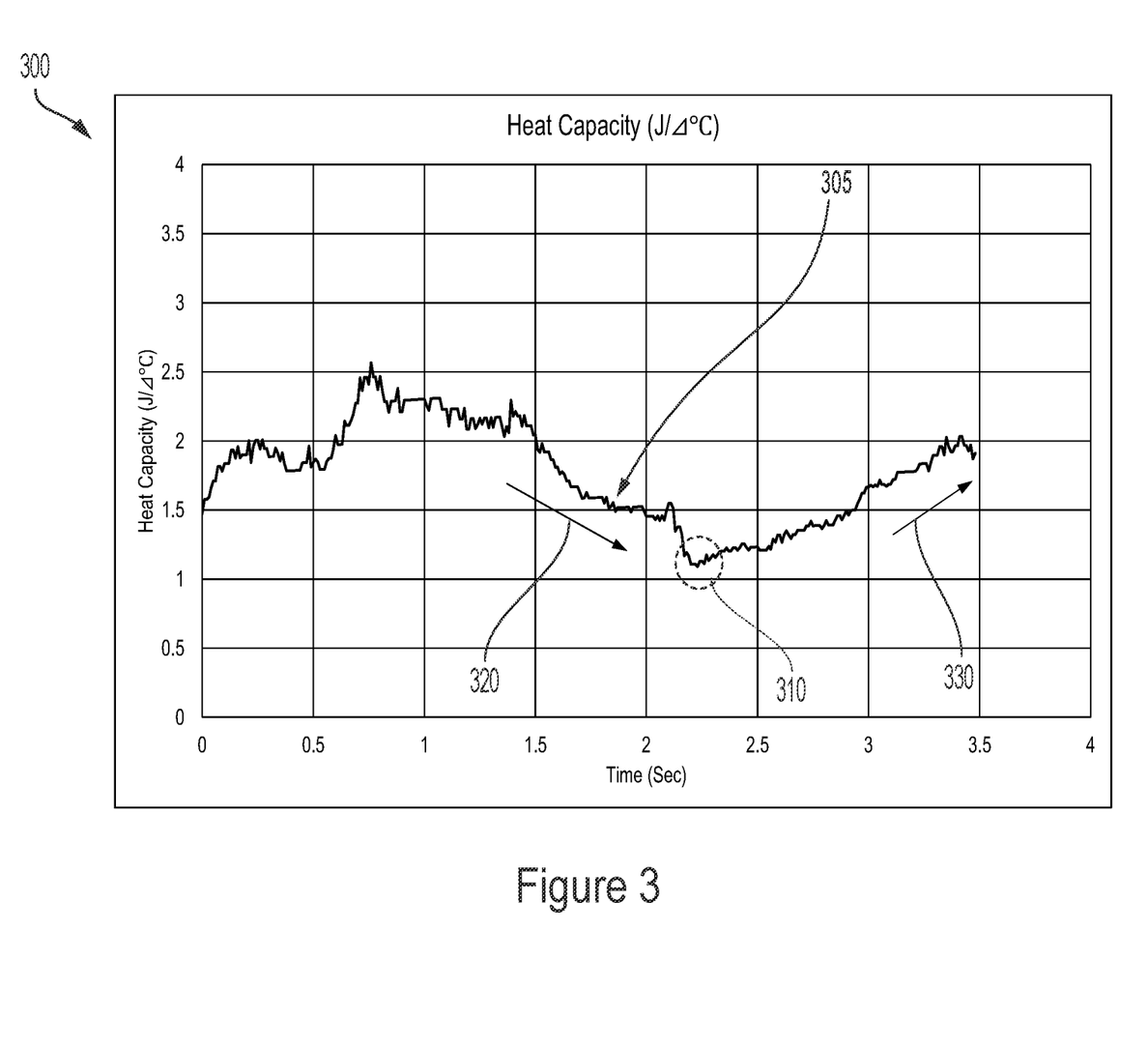
FIG. 3 is a graph showing heat capacity of the biological tissue (in Joule/degree C) as a function of time (in seconds) during a biological tissue cutting procedure using an ultrasonic end-effector.

For example, FIG. 3 is a graph 300 showing a rate of change in the heat capacity of the biological tissue during a biological tissue cutting procedure using an ultrasonic end-effector. Without wishing to be bound by theory, the heat capacity of the end-effector is greater than that of the biological tissue on which the procedure is being performed. Thus, during a biological tissue cutting procedure, the heat capacity is expected to increase once the biological tissue is cut because the target of the procedure changes from being the biological tissue to being the end-effector. Moreover, during the procedure, it is expected that the change in the mass of the biological tissue during the procedure because of water evaporation causes the heat capacity of the biological tissue to change. Thus, during a biological tissue cutting procedure using an ultrasonic end-effector, the rate of change in the heat capacity of the biological tissue (in J/deg C per sec shown at 305) changes from decreasing in one region, as shown by the arrow 320 (for the time period from about 1.25 secs to about 3 secs) to increasing in a second region, as shown by the arrow 330 (for the time period from about 3 secs to about 4.25 secs). The inflection point 310 occurs when the rate of change in the heat capacity of the biological tissue 320 changes from a decreasing rate to an increasing rate. This inflection point 310 is indicative of the ultrasonic vibration target changing from the biological tissue to the pad of end-effector and corresponds to the completion of the cutting process.

Thus, in some embodiments, the completion of the procedure may be determined when the heat capacity of the biological tissue changes in a certain way, e.g., when a rate of change in the heat capacity of the biological tissue changes from decreasing to increasing.

In such embodiments, once the calculation unit 46 determines that the rate of change in the heat capacity of the biological tissue has reached the inflection point 310 and is at this local minima (i.e., the slope of the heat capacity curve relative to time has changed from negative to positive), the processor 32 may cause the control unit 40 to cut off power provided to the instrument 2 by the power source 44 regardless of whether the clinician continues to input control signals for the electrical power to remain ON.

One drawback of using a change in rate of change in the heat capacity of the biological tissue for end-point detection occurs in situations where the procedure is performed under a fluid. In such situations, the change in rate of change in the heat capacity may not be as sharp as desirable for being able to reliably detect the end-point of the procedure. This is because in the presence of fluid, the target of the procedure after the completion of the procedure becomes the fluid. Without wishing to be bound by theory, the heat capacity of the surrounding fluid may be larger than that of the biological tissue because of the presence of water.

Figures 4A, 4B:
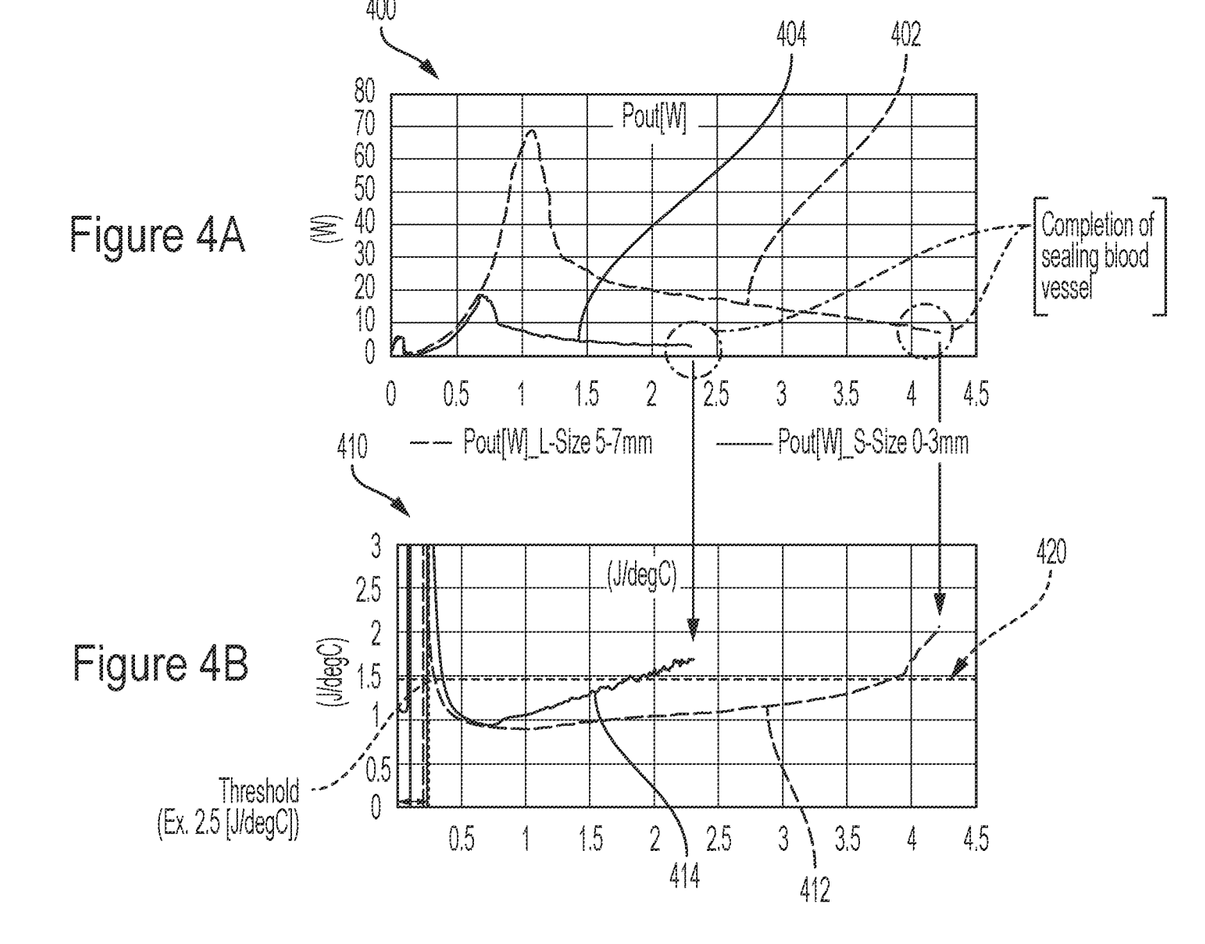
FIGS. 4A and 4B are graphs of time-dependent parameters during a high frequency sealing procedure and showing output power (in watts) as a function of time (in seconds) (FIG. 4A) and showing heat capacity of the biological tissue (in Joule/degree C) as a function of time (in seconds) (FIG. 4B).

Alternatively then, the end-point of a procedure may also be determined when the heat capacity of the biological tissue reaches a preset threshold value. FIGS. 4A and 4B, for example, are graphs showing change in heat capacity during a blood vessel sealing procedure using a high frequency electric energy end-effector performed under water for two different blood vessel sizes. In FIG. 4A, graph 400 shows the power (in watts) as a function of time for a blood vessel with a diameter of 5 to 7 mm (categorized as large and shown at 402) and for a blood vessel with a diameter of 1 to 3 mm (categorized as small and shown at 404). In FIG. 4B, graph 410 shows the heat capacity (in joules/degree Celsius) as a function of time for the same sized blood vessels, i.e., a blood vessel with a diameter of 5 to 7 mm (categorized as large and shown at 412) and for a blood vessel with a diameter of 1 to 3 mm (categorized as small and shown at 414). As seen in FIGS. 4A and 4B, the value of the heat capacity increases above a threshold 420 as the sealing process continues, and remains above the threshold for a certain amount of time indicating that the sealing process has been completed. The graphs 400,410 have been annotated showing how the power in FIG. 4A correlates to the heat capacity in FIG. 4B. In the example shown in FIGS. 4A and 4B, the threshold value of the heat capacity is 2.5 J/DegC.

In such embodiments, once the heat capacity (as estimated at the calculation unit 46) reaches the preset value, the processor 32 may cause the control unit 40 to cut off power provided to the instrument 2 by the power source 44 regardless of whether the clinician continues to input control signals for the electrical power to remain ON.

Thus, in embodiments where the end-effector is an ultrasonic cutting tool, the processor 32 causes the power supplied to the end-effector to be cut off when the calculation unit 46 determines that the heat capacity of the biological tissue being cut has reached a certain preset value or that the rate of change in heat capacity of the biological tissue has reached a local minima. Similarly, in embodiments, where the end-effector is a high frequency sealing tool, the processor 32 causes the power supplied to the end-effector to be cut off when the calculation unit 46 determines that the heat capacity of the biological tissue being sealed has reached a certain preset value or that the rate of change in heat capacity of the biological tissue has reached a local minima.

The heat capacity of the biological tissue is determined by computing a ratio of energy input to the end-effector over a sampling interval to a change in temperature of the biological tissue over that sampling interval. In some embodiments, the heat capacity of the biological tissue is determined or computed continuously during the procedure. Thus, a rate of change in heat capacity of the biological tissue may be determined during the procedure in real-time. Those of skill in the art will appreciate that the presently described determination of the state of the biological tissue during a procedure does not require additional sensors and, advantageously, allows for real-time determination of the end-point of the procedure, thereby improving patient safety as well as procedure efficiency.

In some embodiments, the temperature of the biological tissue (and thus, a change in temperature of the biological tissue) can be determined using signals generated by a temperature sensor placed at the end-effector, e.g., in contact with the biological tissue. However, in embodiments with an ultrasonic end-effector, placing a temperature sensor on or at the end-effector may be difficult because of the vibrations. Moreover, even if such a configuration were to be possible, the vibration may make it difficult to obtain reliable temperature measurements.

Thus, in some embodiments, the temperature (and thus, a change in temperature) of the biological tissue can be determined based on the characteristics of the interaction between the end-effector and the biological tissue during the procedure.

Estimating the Temperature of the End-Effector

The discussion that follows describes various methods for estimating the temperature of the end-effector 10 of the medical device 1.

Regardless of the mechanism by which the electrical power provided to the medical device 1 is converted to heat, the amount of heat produced at the end-effector is proportional to the product of the applied electrical power and the time for which the electrical power is applied. Thus, it is possible to estimate heat produced at the end-effector based on the amount of electrical power provided to the medical device 1, amount of electrical power consumed by the medical device 1, an amount of electrical power applied to the end-effector 10, an amount of electrical power consumed by the end-effector 10, or a combination thereof.

In one embodiment, heat (Q) produced by the end-effector can be calculated as:

$$Q = f(W \cdot t) \quad \text{Equation (1)}$$

where f is a constant specific to the medical device, W is the electrical power input to the medical device, and t is the sampling time. The constant f is indicative of the efficiency with which the medical device converts the inputted electrical energy into heat. The temperature of at the end-effector can then be calculated as:

$$T_C = T_{prev} + \frac{fWt}{mc} \quad \text{Equation (2)}$$

where $T_c$ is the current temperature, $T_{prev}$ is the temperature before the beginning of the sampling time, m is a mass of the portion of the biological tissue surrounding the end-effector and which receives the treatment applied by the end-effector (e.g. by the treatment portion of the end-effector), and c is the specific heat capacity of the treatment portion.

The mass m of the treatment portion is determined based on the size and shape of the end-effector as well as the type of biological tissue on which the procedure is being performed. For example, by the shape and size of the end effector, each end effector is operative on a specific known volume of biological tissue from which a mass m of the treatment portion can then be determined. The specific heat capacity c of the treatment portion depends on the type of the biological tissue on which the procedure(s) are being performed.

The temperature $T_{prev}$ before the beginning of the sampling time is interchangeably referred to herein as the residual temperature, and depends on the power input to the medical device before the sampling time. For example, prior to a first application of power input to the medical device, the temperature of the end effector can be at a temperature of its surroundings, such as the room temperature, a temperature of an autoclave, or the temperature of the patient. Subsequent to completing a first application of power input to the medical device, the medical device will be at some residual temperature that is dependent on the final temperature when power input was being applied and the rate of decay (or cooling) of the end effector. The residual temperature at the end-effector may be calculated using the equation 2. In other words, the estimated current temperature is determined iteratively.

Embodiment 1: Subtracting the Amount of Power Input Prior to the Sampling Time from the Power Input During the Sampling Time The amount of heat generated by the end-effector is based on the power input during a given sampling time. Thus, the estimated current temperature at the end-effector may be more accurately calculated by subtracting the amount of power input prior to the sampling time. Those of ordinary skill in the art will appreciate that at least some of the heat generated by the end-effector is dissipated by conduction through the biological tissue on which the procedure is being performed. Thus, the current temperature of the treatment portion is the sum of the temperature of the treatment portion prior to the sampling time and the rise in the temperature at the end-effector because of the electrical power provided to or consumed by the medical device being converted to heat during the sampling time.

The change in temperature of the treatment portion during the sampling time is calculated as follows:

$$\Delta T = \left( \frac{fW - \frac{T_{prev}}{R_{th}}}{m \times c} \right) / t \qquad \text{Equation (3)}$$

where $R_{th}$ is referred to as thermal resistance of the treatment portion, and is calculated as:

$$R_{th} = \frac{L}{k \times A} \qquad \text{Equation (4)}$$

where k is the thermal conductivity of the treatment portion; A is the contact area between the treatment portion of the end-effector and the body of the biological tissue; and L is the thickness of the treatment portion.

The current temperature at the end-effector can then be estimated as:

$$T = \Delta T + T_{prev} \qquad \text{Equation (5)}$$

In some embodiments, the clinician may initiate the heating of the end-effector after inserting the instrument such that the end-effector is positioned at the treatment portion. As discussed herein, the typical treatment portion is inside the human body. Thus, in such embodiments, the initial temperature of the end-effector at the treatment portion is assumed to be $T_0=37°$ C. (approximately equal to the temperature inside the human body) and used as $T_{prev}$ for the first sampling period. The current temperature is then determinedly by iteratively estimating for each successive sampling period, during the time of the procedure.

In some embodiments, the sampling time may be, for example, 0.1 s, 0.2 s, 0.3 s, 0.4 s, 0.5 s, 0.6 s, 0.7 s, 0.8 s, 0.9 s, 1.0 s, 1.5 s, 2.0 s, 2.5 s, 3 s, 5 s, 10 s, or any other value between any two of these values. Thus, in some embodiments, a clinician may obtain a desired accuracy of the estimated temperature by appropriately selecting the sampling time. In some embodiments, the sampling time is pre-selected based on the end-effector being used such that the accuracy of the estimated current temperature may be adjusted based on the particular procedure being performed. In some embodiments, the sampling time may be preset for the medical device when the medical device is manufactured, in which case the preset value may be programmed into the controller 3 by the user or can be communicated to the controller 3 by the medical device when the medical device is assembled to the controller 3.

In some embodiments, various parameters used for estimating the current temperature such as, for example, the specific heat capacity of the treatment portion, the thermal resistance of the treatment portion, the thermal conductivity of the treatment portion, or the contact area between the body of the biological tissue and the treatment portion, any of which may be provided in, e.g., a look-up table which may include the values of the corresponding parameters for different treatment portions. For example, the look-up table may include the parameters for muscle tissue, adipose tissue, blood vessels, intestinal wall, or other biological tissue types. In such embodiments, estimating the current temperature may include determining the type of biological tissue on which the procedure is being performed, and determining the corresponding parameter values in the look-up table for estimating the current temperature. Alternatively, the procedure name may be used as the basis for entry into the look-up table.

In some embodiments, the data related to the various parameters is a value of the contact area calculated using size and shape of the end-effector, in particular, the treatment portion of the end-effector, and how the end-effector is used (e.g., related to the procedure) and this data is stored in the memory in advance. In addition, as the contact area changes as the end-effector grasps and regrasps biological tissue during the medical procedure, the various parameters can also correspondingly change during the medical procedure, and having the data for the various parameters readily available in memory allows for dynamic updating during the medical procedure.

Embodiment 2: Subtracting Base Ultrasonic Power Consumption from Input Power

In some embodiments, the medical device may include an end-effector that is configured to heat the surrounding biological tissue (i.e., the treatment portion) by application of ultrasonic waves. Ultrasonic waves typically refer to sound waves having a frequency of greater than 20 kHz, and up to several GHz. Vibrations from the ultrasonic waves results in heating the biological tissue surrounding the end-effector of the medical device. Thus, for an end-effector configured to heat the treatment portion by application of ultrasonic waves, Equation (3) can be modified as:

$$\Delta T = \left( \frac{(W - W_{US}) - \frac{k \times A \times T_{prev}}{L}}{m \times c} \right) / t \qquad \text{Equation (3')}$$

where W is power input to the medical device during the procedure over the sampling time t and $W_{US}$ is the power needed to produce ultrasonic waves at the same frequency and intensity as being produced during the procedure assuming there was no load on the end-effector.

In some embodiments, the value of $W_{US}$ can be obtained based on the physics of the end-effector (e.g., using the dimensions, material properties, and other physical characteristics of the end-effector). In some embodiments, the value of $W_{US}$ can be determined using a look-up table that includes the input power needed to generate ultrasonic waves of certain frequencies and intensities.

In some embodiments, the data related to the various parameters is a value of the contact area calculated using size and shape of the end-effector, in particular, the treatment portion of the end-effector, and how the end-effector is used (e.g., related to the procedure) and this data is stored in the memory in advance. In addition, as the contact area changes as the end-effector grasps and regrasps biological tissue during the medical procedure, the various parameters can also correspondingly change during the medical procedure, and having the data for the various parameters readily available in memory allows for dynamic updating during the medical procedure.

Embodiment 3: Factoring Change in Resonance Frequency of the Applied Ultrasonic Waves In medical devices where the end-effector is configured to heat the surrounding biological tissue by application of ultrasonic waves, when performing the procedure there may be instances when the parts of the surrounding biological tissue may adhere to or coagulate around the end-effector. Such adhesion or coagulation may result in reduction in the resonance frequency of the end-effector because of the change in physical characteristics of the end-effector. The decrease in resonance frequency of the end-effector causes a reduction in kinetic energy of the end-effector, thereby reducing the energy consumption of the end-effector.

Thus, the estimate of the current temperature at the end-effector determined, e.g., in Embodiment 2 described herein, may be further improved in some instances by factoring the reduction in resonance frequency of the end-effector. This may be particularly applicable when the treatment portion interacts with biological tissue(s) that are susceptible to adhesion to the end-effector or coagulation around the end-effector.

In such instances, Equation (3') is further modified as:

$$\Delta T = \left( \frac{(W - W_{US}) \times \frac{f_r}{f_{r0}} - \frac{k \times A \times T_{prev}}{L}}{m \times c} \right) / t \quad \text{Equation (3")}$$

where $f_r$ is the current resonance frequency of the end-effector during the sampling period, and $f_{r0}$ is the base resonance frequency of the end-effector.

It will be further appreciated that in instances where the end-effector is configured to grasp a portion of biological tissue when performing the procedure, the grasping force may affect the mode of vibration, and thus, may affect the estimate of the current temperature. However, it will be apparent to those of ordinary skill in the art that any change in resonance frequency or mode of vibration of the end-effector during the procedure is measurable and is factored into Equation (3"). Moreover, measuring the current resonance frequency during a procedure is well-understood in the art. For example, the initial resonant frequency of the device can be determined by the composition of the material generating the ultrasonic (e.g., lead zirconate titanate, PZT) and the end effector. The resonance frequency may be, e.g., about 47 kHz in some embodiments. The resonance frequency during the treatment is dependent on the impedance of the end-effector, and thus, can be estimated by, e.g., impedance matching. At that time, the frequency with the lowest impedance is determined as the current resonance point for the purposes of Equation (3").

Various parameters used in estimating the current temperature in accordance with the present disclosure, such as, for example, k, L, A, m, and c, are determined based on the particular end-effector, particular procedure being performed, and the particular biological tissue being treated. Additionally, features of the treatment portion (such as area, thickness, volume, etc.) and the contact area between the body of the biological tissue and the treatment portion are determined based on the physical characteristics of the end-effector (such as the size and shape). Parameters such as thermal conductivity and specific heat capacity for various materials for the treatment portion as well as for particular biological tissues are well-known in the art and those of ordinary skill in the art will appreciate that appropriate modifications to those parameters may be needed based on the particular use case.

Figure 5A:
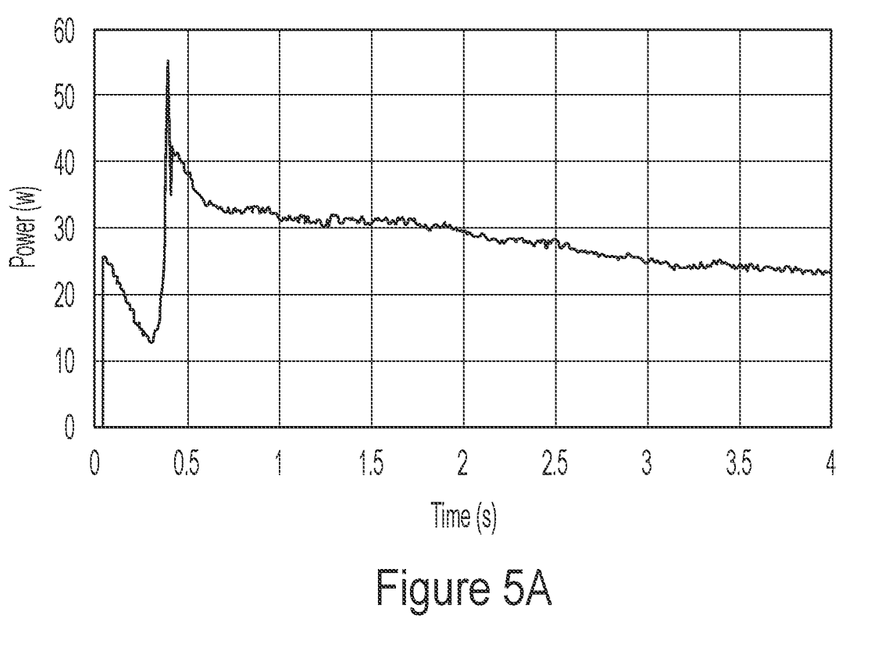
FIG. 5A shows an example of the measured value of power (in watts) outputted by a generator connected to an end-effector as a function of time (in seconds) and FIG. 5B. shows a comparison between the estimated temperature (in Celsius) of the end-effector calculated (using the methods disclosed herein) and the temperature (in Celsius) of the end-effector determined by thermography as a function of time (in seconds).
Figure 5B:
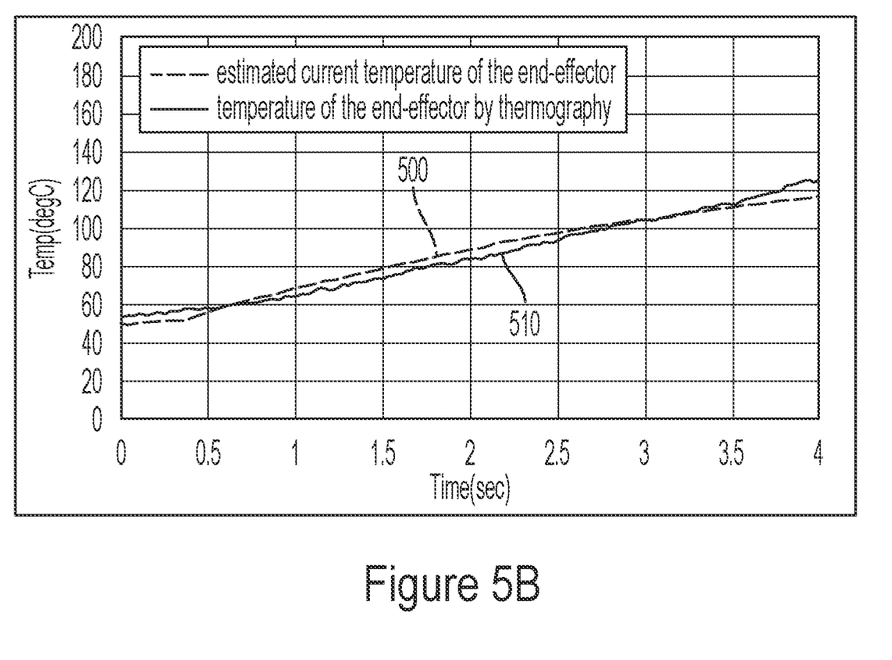

FIG. 5A is a graph showing an example of the measured value of power (in watts) as a function of time (seconds) that is outputted by a generator connected to an end-effector. For this example, the parameters of the end-effector are: m=1.5 g, c=0.585 J/gK, k=7.5 W/mK, A=0.0000075 m², and L=0.0015 m. FIG. 5B is a graph of temperature (in degrees Celsius) as a function of time (seconds) and shows a comparison between the estimated temperature of the end-effector calculated using Equations (5) and (3") (see 500 in FIG. 5B) and the temperature of the end-effector determined by thermography (see 510 in FIG. 5B). As can be seen in FIG. 5B, the estimated temperature based on the method disclosed herein tracks closely with the temperature determined by thermography.

Controlling a Medical Device for Treating a Biological Tissue

Accurate estimation of the end-point of a procedure is important for preventing damage to the surrounding biological tissue as well as for improving efficiency of the procedure is being performed. Thus, once the end-point of the procedure is determined to have reached, in some embodiments, the power input to the medical device may be regulated to ensure that the biological tissue is not overheated or the surrounding biological tissue is not cut, thereby enhancing patient safety as well as procedure efficiency.

In one aspect, a method for controlling a medical device for treating a biological tissue may include estimating a heat capacity of the biological tissue, and determining a state of the biological tissue based on the determined state of the biological tissue. The medical device is controlled based on the determined state of the biological tissue.

Figure 6:
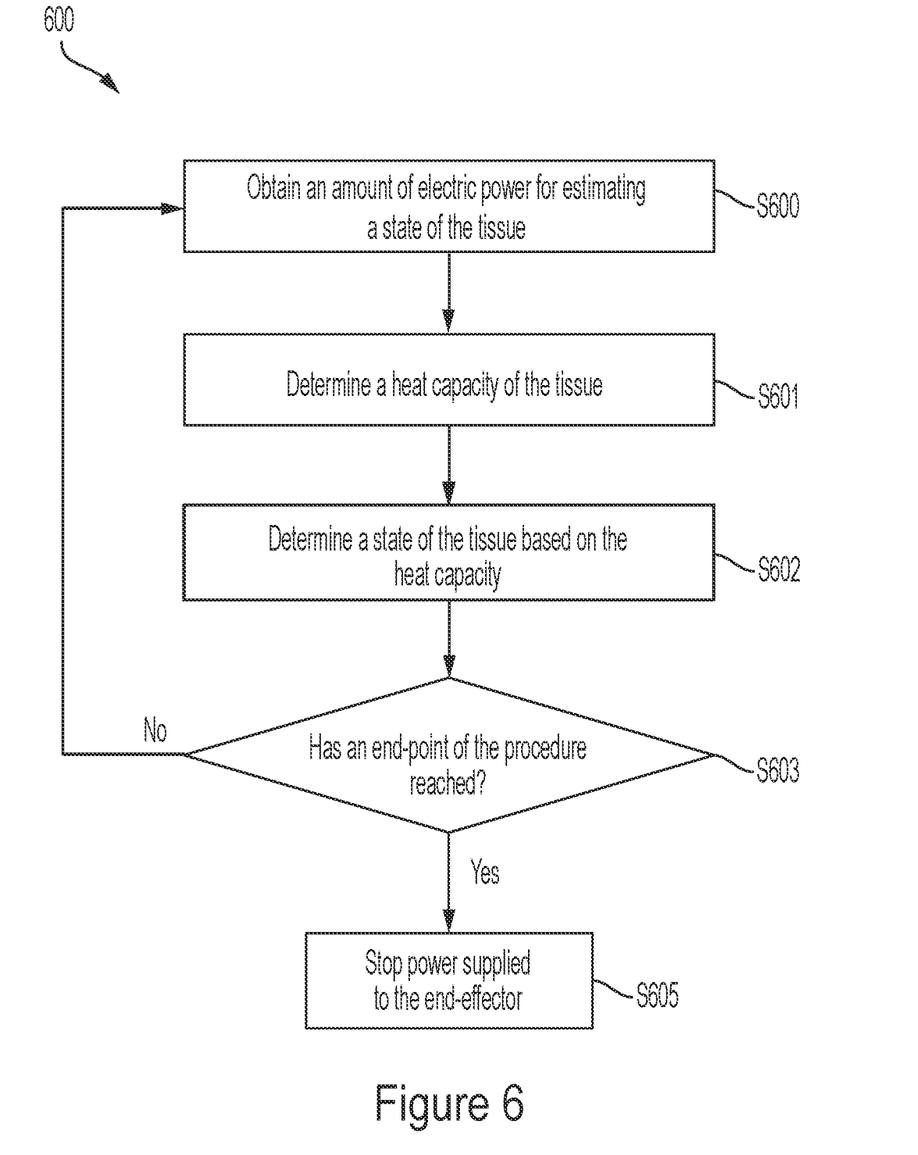
FIG. 6 shows a flow chart for a process of determining an end-point of a procedure, in accordance with an embodiment of the present disclosure.

FIG. 6 shows a flow chart for a process of controlling a medical device for treating a biological tissue, in accordance with some embodiments. The process shown in FIG. 6 relates both to the steps for control of a controller and to the steps in a procedure.

In an example embodiment, a method 600 for controlling a medical device includes at S600, obtaining an amount of electric power for estimating a state of the tissue. The energy input to the end-effector of the medical device may be determined by integrating power input to the end-effector over the sampling interval, for example, the amount of electric power as obtained at S600. Thus, for a sufficiently small interval, the energy input to the end-effector may be a product of the sampling interval and the power input to the end-effector. The power input to the end-effector may be, for example, a product of the voltage applied to a piezo actuator of an ultrasonic end-effector and the current drawn by the piezo actuator. In another example, the power input to the end-effector may be a product of the voltage applied to a high frequency electric energy end-effector and the current drawn by the end-effector.

At S601, a heat capacity of the biological tissue is determined. Any one of the methods described herein may be used, such as estimating the heat capacity of the biological tissue. For example, the heat capacity of the biological tissue may be determined by computing a ratio of energy input to an end-effector of the medical device over a sampling interval to a change in temperature of the biological tissue over that sampling interval. The sampling interval may be, for example, about 0.1 s, about 0.2 s, about 0.3 s, about 0.4 s, about 05. s, about 0.6 s, about 0.7 s, about 0.8 s, about 0.9 s, about 1.0 s, about, 1.2 s, about 1.4 s, about 1.6 s, about 1.8 s, about 2.0 s, about 2.5 s, about 3.0 s, or any other duration between any two of these values.

The change in temperature during the sampling interval may be estimated using any of the methods disclosed herein. For example, the change in temperature may be computed using any of the Equations (3), (3') or (3") depending on the type of end-effector.

At S602, a state of the biological tissue is determined based on the heat capacity. Any methods described herein may be used for determining the state of the biological tissue. For example, the state of the biological tissue may be determined based on a rate of change in the heat capacity of the biological tissue in an embodiment. In some embodiments, the state of the biological tissue may be determined based on a value of the heat capacity, and more particularly, on a comparison of the value of the heat capacity with a predetermined threshold value.

At S603, the state of the biological tissue is compared to a state of the biological tissue at an end-point of the procedure and it is determined whether the end-point of the procedure has been reached, e.g., completion of the procedure. For example, the end-point of the procedure may correspond to the inflection point 310 shown in FIG. 3. The end-point of the procedure is dependent on the particular procedure being performed as well as on the type of end-effector being used for performing that procedure. If, at S603 the end-point has not been reached, the method reverts back to S600. In other words, if, at S603, the determination of whether the end-point of the procedure has been reached is NO, the then method reverts back to S600 and repeats the subsequent process. On the other hand, if at S603 the end-point has reached, the method moves to S605 where power supplied to the end-effector is stopped.

Thus, in embodiments where the end-effector is an ultrasonic tissue cutting tool, the state of the biological tissue at the end-point of the procedure is that the biological tissue is cut. In such embodiments, the end-point may be determined based on a rate of change in the heat capacity, and more particularly, based on a change in the rate of the change in the heat capacity of the biological tissue. Thus, for an ultrasonic cutting tool end-effector, the cutting is determined to be complete when a rate of change of the heat capacity of the biological tissue changes from decreasing to increasing.

Similarly, in embodiments where the end-effector is a high frequency electric energy sealing tool, the state of the biological tissue at the end-point of the procedure is that the biological tissue is sealed. In such embodiments, the end-point of the procedure may be determined by comparing the heat capacity of the biological tissue with a predetermined threshold value. For example, the a blood vessel is considered to be sealed when the heat capacity of the blood vessel exceeds a predetermined value, and in particular, when the heat capacity of the blood vessel exceeds the predetermined value for more than a certain period of time.

If, at S603, it is determined that the end-point of the procedure has reached, at S605, the power supplied to the end-effector is stopped, so as to stop the procedure. Such automatic stoppage of the procedure by cutting off power to the end-effector when it is determined that the end-point of the procedure is reached ensures that the biological tissue not overheated or that excess biological tissue is not cut. Advantageously, the automatic stoppage also saves the clinician's time by preventing the clinician from continuing the procedure after the end-point of the procedure has reached.

In some embodiments, the clinician is provided with a confirmation or alert that the procedure is complete and the power supplied to the end-effector is cut-off. For example, once the power supplied to the end-effector is stopped, an audio, visual, audiovisual and/or haptic feedback is provided to the clinician indicating that the procedure is complete, thereby allowing the clinician to move to the next procedure.

If, at S603, it is determined that the end-point of the procedure has not been reached, the method continues from S600 to obtain the amount of electric power for estimating a state of the tissue. In other words, in accordance with the method illustrated in FIG. 6, the determination of the heat capacity of the biological tissue and the determination of the state of the biological tissue are performed repeatedly for several sampling intervals until the end-point of the procedure is reached. Accordingly, S600, S601 and S602 may be performed 1, 2, 3, 4, 5, 6, 7, 8, 9, 10, 12, 14, 16, 18, 20, 25, 30, 35, 40, 50, 60, 70, 80, 100, 120, 140, 160, 180, 200, 250, 300, 350, 400, 500, or any number of times between any two of these numbers depending on factors such as, for example, the procedure being performed, the size of the biological tissue on which the procedure is being performed and the selected sampling interval.

Thus, by accurately estimating the end-point of the procedure based on an estimated heat capacity of the biological tissue on which the procedure is being performed, patient safety and clinician efficiency is improved. Moreover, because the end-point detection described herein can be performed by measuring parameters without any additional sensors, existing hardware can be suitably modified to allow implementation of the presently disclosed embodiments.

Although the present invention has been described in connection with the above exemplary embodiments, it will be appreciated by those skilled in the art that additions, deletions, modifications, and substitutions not specifically described may be made without department from the spirit and scope of the invention as defined in the appended claims.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The singular forms "a," "an," and "the" include plural referents unless the context clearly dictates otherwise. Thus, for example, reference to "a plunger component" includes reference to one or more plunger components, and reference to "the magnet" includes reference to one or more magnets.

In one or more aspects, the terms "about," "substantially," and "approximately" may provide an industry-accepted tolerance for their corresponding terms and/or relativity between items, such as from less than one percent to five percent.

As used herein, the term "substantially" refers to the complete or nearly complete extent or degree of an action, characteristic, property, state, structure, item, or result.

It is to be understood that a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 cm" should be interpreted to include not only the explicitly recited values of about 0.5 cm to about 10.0 cm, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this disclosure belongs. Although any methods, devices and materials similar or equivalent to those described herein can be used in the practice or testing of the disclosure, representative methods, devices, and materials are described below.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the Internet or a local area network (LAN). Many modifications may be made to this configuration without departing from the scope or spirit of the claimed subject matter.

Although the detailed description contains many specifics, these should not be construed as limiting the scope of the subject technology but merely as illustrating different examples and aspects of the subject technology. It should be appreciated that the scope of the subject technology includes some embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method for controlling a medical device for treating a biological tissue, the method comprising:
    obtaining an amount of electric power for estimating a state of the tissue;
    determining an in-process heat capacity of the biological tissue during a time period of application of applied energy to the biological tissue, wherein the applied energy is ultrasonic energy or electrical energy;
    determining a state of the biological tissue based on the in-process heat capacity; and
    controlling the medical device based on the state of the biological tissue,
    wherein the medical device includes an end-effector configured to operate on the biological tissue,
    wherein determining the in-process heat capacity of the biological tissue includes determining a ratio of energy input to the end-effector over a sampling interval to a change in temperature of the biological tissue over that sampling interval, and
    wherein the change in temperature of the biological tissue is determined by:
        estimating, based on a first set of parameters, a residual energy associated with (i) a prior amount of electrical power provided to the medical instrument, (ii) a prior amount of electrical power consumed by the medical instrument, (iii) a prior amount of electrical power applied to the end-effector, (iv) a prior amount of electrical power consumed by the end-effector, or (v) a combination thereof;
        determining, based on the first set of parameters, a change in energy of the end-effector based on (i) a current amount of electrical power provided to the medical instrument, (ii) a current amount of electrical power consumed by the medical instrument, (iii) a current amount of electrical power applied to the end-effector, (iv) a current amount of electrical power consumed by the end-effector, or (v) a combination thereof;
        estimating a residual temperature of the end-effector associated with the residual energy; and
        determining a change in temperature of the end-effector associated with the change in energy.

2. The method according to claim 1, wherein the change in temperature of the biological tissue is further determined by:
    estimating a residual energy associated with a prior application of base energy to the end-effector based on a first set of parameters;
    estimating an amount of electric power that is converted to heat at the end-effector based on the first set of parameters; and
    estimating a current temperature at the end-effector based on: (i) the residual energy, (ii) the amount of electric power provided to the end-effector, and (iii) a time for which the electric power is provided to the end-effector.

3. The method according to claim 2, wherein the first set of parameters includes one or more of a mass of a treatment portion of the end-effector, a shape of the treatment portion of the end-effector, a size of the treatment portion of the end-effector, and a specific heat of the treatment portion of the end-effector.

4. The method according to claim 1, wherein determining the state of the biological tissue includes determining the state of the biological tissue based on a change in the in-process heat capacity.

5. The method according to claim 4, wherein the medical device includes an end-effector configured to heat the biological tissue,
    wherein determining the state of the biological tissue includes detecting an end-point of a procedure being performed on the biological tissue by the end-effector, and
    wherein controlling the medical device includes stopping application of applied energy to the biological tissue upon detection of the end-point of the procedure.

6. The method according to claim 5, wherein the applied energy is ultrasonic energy and the end-effector is configured to heat the biological tissue by providing ultrasonic vibration to the biological tissue,
    wherein the end-point of the procedure includes completion of cutting of the biological tissue, and
    wherein the completion of cutting of the biological tissue is determined when a rate of change of the heat capacity of the biological tissue changes from a decreasing rate to an increasing rate.

7. The method according to claim 5, wherein the applied energy is ultrasonic energy and the end-effector is configured to heat the biological tissue by providing ultrasonic vibration to the biological tissue,
    wherein the end-point of the procedure includes completion of cutting of the biological tissue, and
    wherein the completion of cutting of the biological tissue is determined when a rate of change of the heat capacity of the biological tissue exceeds a heat capacity threshold value.

8. The method according to claim 5, wherein the applied energy is ultrasonic energy and the end-effector is configured to heat the biological tissue by providing ultrasonic vibration to the biological tissue,
    wherein the end-point of the procedure includes completion of cutting of the biological tissue, and
    wherein the completion of cutting of the biological tissue is determined when (i) a rate of change of the heat capacity of the biological tissue changes from a decreasing rate to an increasing rate and (ii) the rate of change of the heat capacity of the biological tissue exceeds a heat capacity threshold value.

9. A controller for a medical device for treating a biological tissue, the controller comprising a processor configured to:
    obtain an amount of electric power for estimating a state of the tissue;
    determine an in-process heat capacity of the biological tissue during a time period of application of applied energy to the biological tissue, wherein the applied energy is ultrasonic energy or electrical energy;
    determine a state of the biological tissue based on the in-process heat capacity; and
    control the medical device based on the state of the biological tissue,
    wherein the medical device includes an end-effector configured to operate on the biological tissue,
    wherein determining the in-process heat capacity of the biological tissue includes determining a ratio of energy input to the end-effector over a sampling interval to a change in temperature of the biological tissue over that sampling interval, and
    wherein the change in temperature of the biological tissue is determined by:
        estimating, based on a first set of parameters, a residual energy associated with (i) a prior amount of electrical power provided to the medical instrument, (ii) a prior amount of electrical power consumed by the medical instrument, (iii) a prior amount of electrical power applied to the end-effector, (iv) a prior amount of electrical power consumed by the end-effector, or (v) a combination thereof;

determining, based on the first set of parameters, a change in energy of the end-effector based on (i) a current amount of electrical power provided to the medical instrument, (ii) a current amount of electrical power consumed by the medical instrument, (iii) a current amount of electrical power applied to the end-effector, (iv) a current amount of electrical power consumed by the end-effector, or (v) a combination thereof:

estimating a residual temperature of the end-effector associated with the residual energy; and determining a change in temperature of the end-effector associated with the change in energy.

10. The controller according to claim 9, wherein the change in temperature of the biological tissue is further determined by:

estimating a residual energy associated with a prior application of base energy to the end-effector based on a first set of parameters;

estimating an amount of electric power that is converted to heat at the end-effector based on the first set of parameters; and estimating a current temperature at the end-effector based on: (i) the residual energy, (ii) the amount of electric power provided to the end-effector, and (iii) a time for which the electric power is provided to the end-effector.

11. The controller according to claim 9, wherein the first set of parameters includes one or more of a mass of a treatment portion of the end-effector, a shape of the treatment portion of the end-effector, a size of the treatment portion of the end-effector, and a specific heat of the treatment portion of the end-effector.

12. The controller according to claim 9, wherein determining the state of the biological tissue includes determining the state of the biological tissue based on a change in the in-process heat capacity.

13. The controller according to claim 12, wherein the medical device includes an end-effector configured to heat the biological tissue, wherein determining the state of the biological tissue includes detecting an end-point of a procedure being performed on the biological tissue by the end-effector, and wherein controlling the medical device includes stopping application of applied energy to the biological tissue upon detection of the end-point of the procedure.

14. The controller according to claim 13, wherein the applied energy is ultrasonic energy and the end-effector is configured to heat the biological tissue by providing ultrasonic vibration to the biological tissue, wherein the end-point of the procedure includes completion of cutting of the biological tissue, and wherein the completion of cutting of the biological tissue is determined when a rate of change of the heat capacity of the biological tissue changes from a decreasing rate to an increasing rate.

15. The controller according to claim 13, wherein the applied energy is ultrasonic energy and the end-effector is configured to heat the biological tissue by providing ultrasonic vibration to the biological tissue, wherein the end-point of the procedure includes completion of cutting of the biological tissue, and wherein the completion of cutting of the biological tissue is determined when a rate of change of the heat capacity of the biological tissue exceeds a heat capacity threshold value.

16. The controller according to claim 13, wherein the applied energy is ultrasonic energy and the end-effector is configured to heat the biological tissue by providing ultrasonic vibration to the biological tissue, wherein the end-point of the procedure includes completion of cutting of the biological tissue, and wherein the completion of cutting of the biological tissue is determined when (i) a rate of change of the heat capacity of the biological tissue changes from a decreasing rate to an increasing rate and (ii) the rate of change of the heat capacity of the biological tissue exceeds a heat capacity threshold value.

* * * * *